United States Patent [19]
Sipe et al.

[11] Patent Number: 5,536,640
[45] Date of Patent: *Jul. 16, 1996

[54] LIGAND/ANTI-LIGAND ASSAYS FOR ADHERENT PROTEINS

[75] Inventors: Jean D. Sipe, Roslindale; Greta Knapschaefer, Malden; Wayne A. Gonnerman, Waltham; Carl Franzblau, Newton Highlands, all of Mass.

[73] Assignee: Trustees of Boston University, Boston, Mass.

[*] Notice: The term of this patent shall not extend beyond the expiration date of Pat. No. 5,262,303.

[21] Appl. No.: 146,574

[22] Filed: Oct. 29, 1993

Related U.S. Application Data

[63] Continuation of Ser. No. 595,451, Oct. 11, 1990, Pat. No. 5,262,303.

[51] Int. Cl.⁶ .................................................. G01N 33/53
[52] U.S. Cl. ...................... 435/7.5; 435/7.92; 436/71; 436/518; 436/825
[58] Field of Search ............... 435/7.5, 7.1, 7.8, 435/7.92; 436/71, 518, 533, 534, 536, 531, 526, 825, 826

[56] References Cited

U.S. PATENT DOCUMENTS

| | | | |
|---|---|---|---|
| 4,362,531 | 12/1982 | de Steenwinkel et al. | 436/512 |
| 4,658,022 | 4/1987 | Knowles et al. | 530/402 |
| 4,677,057 | 6/1987 | Curtiss et al. | 435/7.95 |
| 4,782,014 | 11/1988 | Serban et al. | 435/7.5 |
| 4,877,746 | 10/1989 | Jansson et al. | 436/518 |
| 5,262,303 | 11/1993 | Sipe et al. | 435/7.5 |

OTHER PUBLICATIONS

J. Sipe et al., "Direct Binding Enzyme–Linked Immunosorbent Assay (ELISA) For Serum Amyloid A (SAA)", *Journal of Immunogical Methods*, vol. 125 (1989), pp. 125–135.

J. Sipe et al. "Normal Lipoproteins Inhibit Binding Of SAA–Rich Lipoproteins To Polyvinylchloride Surfaces", *J.B. Natvig*, (1991), pp. 894–897.

Benditt et al., *Meth. Enzymol.*, 163:510 (1988).

Benditt and Eriksen, *J. Pathol.*, 64:231 (1971).

Benson and Cohen, *Arthritis Rheum.*, 22:36 (1979).

Chambers and Whicher, *J. Immunol. Methods*, 59:95 (1983).

Dubois and Malmendier, *J. Immunol. Methods*, 112:71 (1988).

Erikson and Benditt, *Meth. Enzymol.*, 128:311 (1986).

Glenner et al., *N. England Journal Med.*, 302:1283 (1980).

Godenir et al., *J. Immunol. Methods*, 83:217 (1985).

Marhaug et al., *Clin. Exp. Immunol.*, 50:382 (1982).

Marhaug, *Scand. J. Immunol.*, 18:329 (1983).

Pepys et al., *Adv. Immunol.*, 34:190–199 (1983).

Pepys and Baltz, *Adv. Immunol.*, 34:141 (1983).

Ram et al., *Int. Arch. Allergy*, 34:269 (1968).

Sipe et al., *Br. Jo. Exp. Path.*, 57:582 (1976).

van Rijswijk, Amyloidosis, *Ph.D. Thesis*, University of Gronigen, The Netherlands (1981).

Zuckerman and Surprenant, *J. Immunol. Methods*, 92:37 (1986).

Primary Examiner—Christine M. Nucker
Assistant Examiner—Donna C. Wortman
Attorney, Agent, or Firm—David G. Conlin; Linda M. Buckley

[57] ABSTRACT

The present invention provides ligand/anti-ligand assays for detecting and/or measuring adherent proteins, including lipophilic serum or plasma proteins, such as serum amyloid A (SAA) and apolipoprotein Al (apoAl); cytokines such as IL-1 beta, IL-6, and TNF alpha; pentraxins, such as CRP; and globular serum or plasma proteins such as albumin.

20 Claims, 9 Drawing Sheets

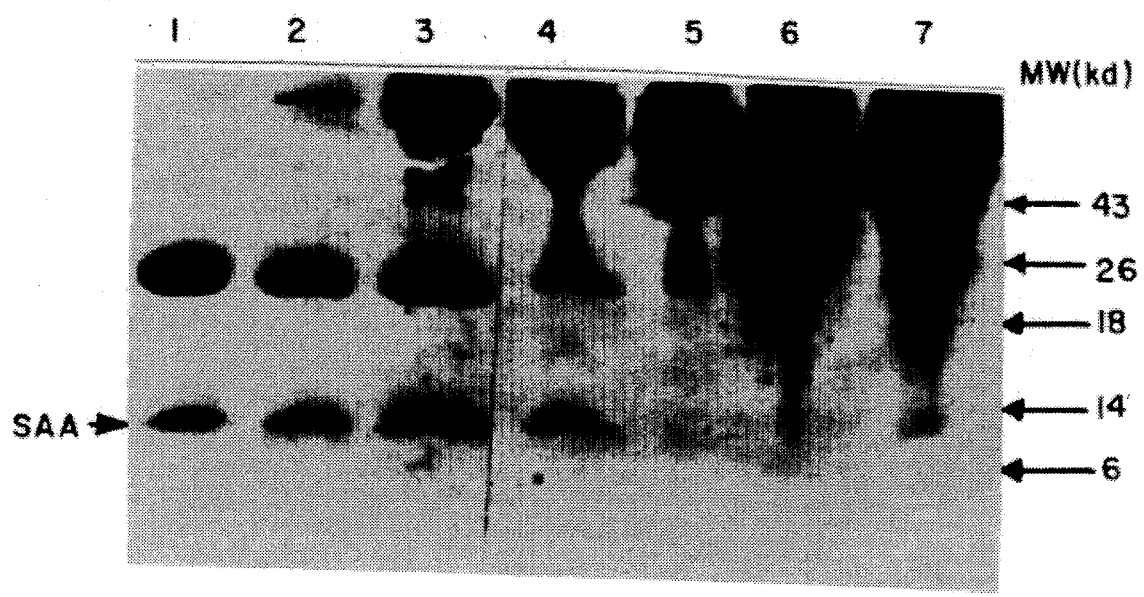
FIG. IA
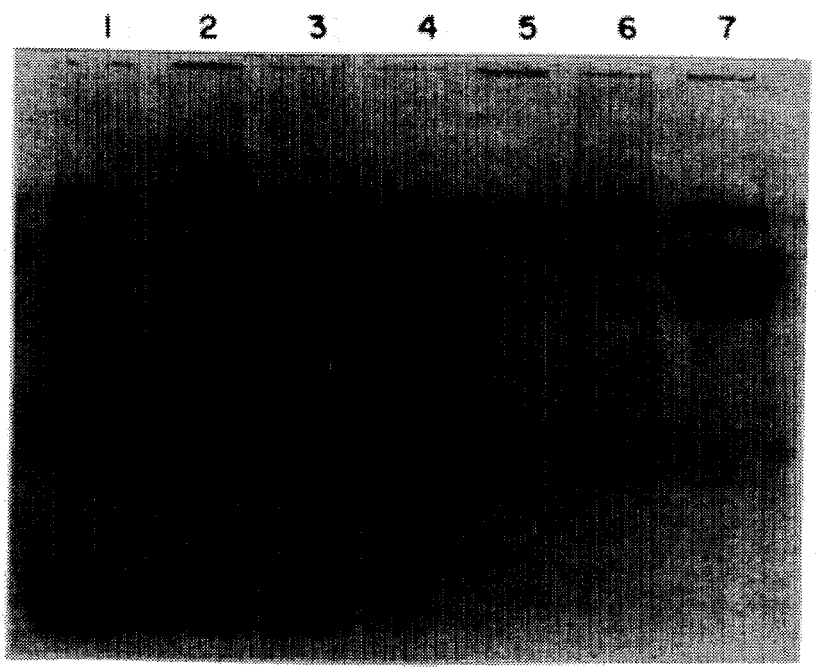
FIG. IB

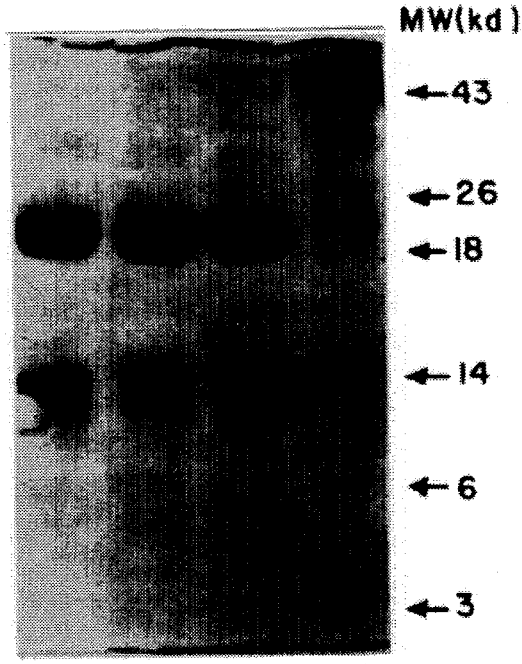
FIG. IC
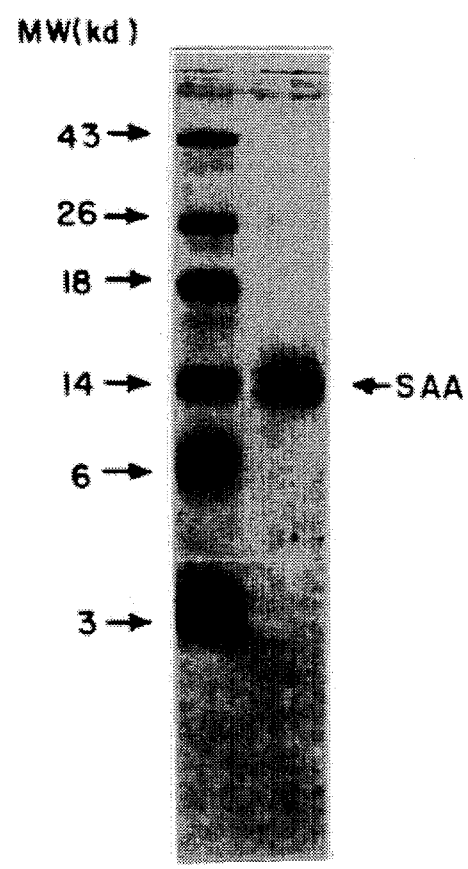
FIG. ID

LIGAND/ANTI-LIGAND ASSAYS FOR ADHERENT PROTEINS

This is a continuation of application Ser. No. 07/595,451, now U.S. Pat. No. 5,262,303, filed on Oct. 11, 1990.

BACKGROUND OF THE INVENTION

The present invention relates to ligand/anti-ligand assays for detection and measurement of adherent proteins, including lipophilic serum and plasma proteins, cytokines, globular serum and plasma proteins, and pentraxins. Assays of the present invention are particularly useful for detection and measurement of serum amyloid A, apolipoprotein Al, apolipoprotein B, CRP, IL-1 beta, TNF alpha, albumin and similar adherent proteins.

Biological fluids such as plasma and serum contain numerous proteins. The presence, absence or concentration of a particular protein may be of interest because, e.g., such data provide information regarding the clinical state of the individual from which the biological fluid was obtained. Accordingly, it is desired to have relatively simple and inexpensive assays to detect the presence of and determine the concentration of such proteins.

By way of example, plasma and serum contain several classes of proteins which are non-covalently linked to lipids. These lipophilic proteins perform a variety of functions, including lipid transport, intercellular communication, and host defense. Medical research has found that in a number of disease states, levels of lipophilic serum and plasma proteins deviate from those found in non-disease states. The significance of these deviations is the subject of active clinical research.

The concentrations of many of the lipophilic serum or plasma proteins change as the physical state of the body changes. For example, the level of serum amyloid A dramatically increases during inflammation; the level of apoliprotein Al decreases during coronary disease, while that of apolipoprotein B is elevated during coronary disease. Clinical measurement of these kinds of proteins will therefore become more important as more is learned about the mechanisms of various disease states.

Accurate and reproducible measurement of lipophilic serum or plasma proteins has historically been difficult. Many factors contribute to these difficulties, such as the existence of multiple forms of the lipophilic proteins and the inherent "stickiness" of the lipophilic proteins.

Organisms frequently contain several molecular forms of a particular lipophilic protein, which differ only slightly in amino acid sequence. These molecular forms are known as isotypes, each of which may in turn may exist in multiple conformational states. Immunological reactivity may vary among isotypes and conformational states of a particular isotype.

Conformational changes are frequently observed in apolipoproteins which accompany the binding of lipid by the apolipoprotein. (Bausserman et al, *J. Biol. Chem.* 258, 10681 (1983); Segrest et al., *Biochemistry* 15, 3187 (1976); Segrest et al., *FEBS Letters* 38, 247 (1974); Morrisett et al, *Biochemistry* 12, 1290 (1973)). It is possible to observe these conformational changes when the protein in serum or plasma is analyzed by immunodiffusion or charge shift immunoelectrophoresis (Linke, *Biochim. Biophys. Acta* 668, 388 (1981)). Treatment with heating, acid, alkali, guanidine hydrochloride and extraction with organic solvents can also induce changes in apolipoprotein conformation. (Sipe et al., Br. *J. Exp. Path.* 57, 582 (1976); Pepys and Baltz, *Adv. Immunol.* 34, 141 (1983); Eriksen and Benditt, *Meth. Enzymol.* 128, 311 (1986); Maciejko, *Clin. Chem.* 28, 199 (1982)).

Moreover, lipophilic proteins are "sticky", i.e., they form non-specific hydrophobic interactions with other molecules of the same structure (also referred to as self association). This stickiness also causes non-specific hydrophobic interactions between the lipophilic proteins and unrelated serum proteins and laboratory vessels. (Franklin, *J. Exp. Med.* 144, 1679 (1976); Marhaug and Husby, *Clin. Exp. Immunol.* 45, 97 (1981); Bausserman et al., op. cit., (1983)). The inherent stickiness of lipophilic proteins causes inaccurate measurements of the proteins in immunoassays.

Three representative lipophilic proteins present in serum and plasma are apolipoprotein Al, apolipoprotein B, and serum amyloid A. Apolipoprotein Al (hereinafter apoAl) is one of the major proteins present in high-density lipoproteins (hereinafter HDL). Apo Al may be a necessary structural component of HDL (H. K. Naito, *J. Clin. Immunoassay* 9, 11 (1986), and it is an activator of lecithin cholesterol acetyl transferase, an enzyme in the pathway which removes cholesterol from peripheral blood. Apolipoprotein B (hereinafter apoB), the principal protein constituent of low density lipoproteins (hereinafter LDL), is active in recognition of cellular receptors for catabolism of LDL. Serum amyloid A (hereinafter SAA) is also associated with HDL, but this lipoprotein plays no known role in lipid transport. SAA is one of the acute phase reactants, i.e., it is present at elevated levels during acute inflammatory states.

ApoAl consists of a single unglycosylated chain of 243 to 245 amino acid residues, which do not include cystine, cysteine, or leucine. Several isotypes of ApoAl exist, and the lipid-free state of the protein has an alpha helical content of 55% which increases to 75% when phoppholipid is bound to the apoprotein. ApoAl is synthesized in liver and intestine.

The clinical importance of ApoAl measurements lies in its utility in assessing coronary artery disease. As stated above, ApoAl levels are decreased in individuals with coronary disease and are therefore of clinical significance. ApoB levels, in contrast, are elevated in coronary disease, and comparative measurement of ApoAl and ApoB levels provides a sensitive clinical profile.

The concentration of SAA in plasma and other biological specimens is also of clinical significance (Rosenthal and Franklin, *J. Clin. Invest.* 55, 746 (1975); Gorevic et al., *Clin. Immunopathol.* 6, 83 (1976); Pepys & Baltz, op. cit., (1983); Sipe, in *Laboratory Diagnostic Procedures in the Rheumatic Diseases*, A. S. Cohen, ed., Grune and Stratton, Orlando (1985), p. 77; Kushner & Mackiewicz, Disease Markers 5, 1 (1986)). There is minimal SAA synthesis during homeostasis, but within a few hours after injury, two major and several minor isoforms of SAA can be detected in plasma high density lipoproteins (hereinafter HDL) (Benditt and Eriksen, *Proc. Natl. Acad. Sci. USA* 74, 4925 (1977); Bausserman et al., *J. Exp. Med.* 152, 641 (1980); Benditt et al., *Meth. Enzymol.* 163, 510 (1988); Strachan et al., *J. Biol. Chem.* 264; 18368 (1989)). The amount and duration of SAA production during the acute phase response to tissue injury and cell necrosis depend upon the type of injury and its magnitude (McAdam et al., *J. Clin. Invest.* 61, 390 (1978); Sipe, in *Rheumatology and Immunology*, A. S. Cohen and J. C. Bennett, eds., Grune and Stratton, Orlando (1986), p. 97).

Synthesis of SAA is regulated by secretory products of the macrophase such as interleukin-1, tumor necrosis factor, and interleukin-6 (Vogel and Sipe, *Surv. Immunol. Res.* 1, 235

(1982); Ganapathi et al., *Biochem. Biophys. Res. Commun.* 157, 271 (1988)). SAA is cleared and/or consumed from plasma more rapidly than most glycosylated acute phase proteins (L. L. Bausserman, in *Amyloidosis*, J. Marrink and M. H. vanRijswijk, eds., Martinus Nijhoff, Amsterdam (1986), p. 337). SAA concentration is thus a useful indicator of the recent production and action of Il-1 and related cytokines.

In the past two decades, SAA has been studied as the precursor of amyloid fibrils, as an apoprotein constituent of HDL, and, most extensively, as an acute phase protein. Because the concentration of circulating SAA is a sensitive, specific and quantitative marker of recent tissue damage and cell necrosis, it is of interest to monitor SAA values in clinical practice. However, despite its potential usefulness, reliable clinical measurement of SAA and many other lipophilic proteins has not been possible. This is in large part due to the physicochemical properties of these proteins.

There are two amphipathic helical regions in SAA, one in the amino terminal portion of the molecule spanning residues 1–24, and the second from residues 50 to 74 (Parmelee et al, *Biochemistry* 21, 3298 (1982)). Dramatic changes in conformation and solubility occur when the carboxyl portion of some isoforms of the SAA molecule is removed by proteolytic cleavage to form amyloid A (AA). AA protein forms insoluble fibrils having the cross beta pleated sheet conformation and accumulating in the extracellular spaces of tissues (Benditt and Eriksen, *J. Pathol.* 65, 231 (1971); Glenner, *N. Eng. J. Med.* 302, 1283 (1980)). The isolated fibrils are reported to be minimally antigenic and immunogenic (Ram et al., *Int. Arch. Allergy* 34, 269 (1968)).

Although the major portion of SAA in plasma may be isolated with HDL proteins after hours of centrifugation in the presence of high concentrations of salt, it has been reported that a portion of plasma SAA is present in the nonlipoprotein fraction of plasma (Marhaug, et al., *Clin. Exp. Immunol.* 50, 382 (1982), Bausserman, personal communication). Because it is not bound to lipids, the SAA in the nonlipoprotein plasma fraction can be expected to have a different conformation from that isolated with HDL proteins. A plasma sample could thus conceivably contain both SAA conformers, i.e., free SAA and HDL-associated SAA. Conformational differences between the conformers can affect the accuracy of immunological assays, since a particular antibody or antiserum may not recognize all of the epitopes exposed in the various conformers. Similar phenomena may also occur because of the existence of more than one isotype of SAA present in the same individual.

The technical difficulties surrounding accurate, reproducible quantification of SAA concentration in plasma and other biological fluids have been widely noted (Marhaug, *Scand. J. Immunol.* 18, 329 (1983); Pepys and Baltz, op. cit., (1983); Godenir et al., *J. Immunol. Methods* 83, 217 (1985); Benditt et al., op. cit., (1988)). It has often been reported that optimal immunochemical measurement requires denaturation and dissociation of SAA from lipids and apolipoproteins. Some laboratories have found that denaturation by heat, acid or alkali increase immunoreactivity and reproducibility of SAA measurements (Sipe et al., op. cit., (1976); van Rijswijk, *Amyloidosis*, Ph.D. Thesis, University of Gronigen, The Netherlands (1981); Eriksen and Benditt, op. cit., (1986). On the other hand, other investigators report that the use of denaturing treatments results in less satisfactory quantification (Benson and Cohen, *Arthritis Rheum.* 22, 36 (1979); Chambers and Whicher, *J. Immunol. Methods* 59, 95 (1983); Marhaug, op. cit. (1983)). The basis for these differing observations is thought to lie in the epitope specificity of the antibodies employed and in the particular type of immunoassay employed (direct or competitive binding radioimmunoassays (RIA) or enzyme-linked immunosorbent assays (ELISA) or radial immunodiffusion).

Purified apoSAA may be measured by any of the traditional methods for measuring proteins. However, methods such as gel scanning, amino acid analysis, or high performance liquid chromatography are expensive and labor intensive and are thus unsuitable for clinical use. Moreover, these methods require purification since serum and plasma contain substances which may interfere with traditional protein assays. Furthermore, measurement of purified SAA may not accurately reflect the levels of the native lipoprotein.

Immunoassays that measure SAA in the native state are highly desirable, since clinical laboratories routinely use these kinds of procedures, and such assays form the basis of a large portion of general clinical literature on many biological ligands. Several immunoassays for SAA have been described (DeBeer et al., 1982, Bausserman et al., 1988, Bensor and Cohen, 1979). However, the known assays of SAA are subject to interference from other plasma constituents and have not proven clinically useful.

Moreover, the known clinically applicable immunoassays are only semi-quantitative, with sensitivities adequate for the high SAA levels observed in acute states such as pneumonia or trauma but inadequate for monitoring SAA in chronic patients. SAA levels in chronic rheumatic patients can be as low as 5–100 µg/ml, and changes in SAA levels of a chronic rheumatic patient as small as 10 to 20 µg/ml can be clinically relevant. Monitoring of chronic patients necessitates, therefore, a more sensitive assay than has previously been available.

Finally, inflammatory stimulation stimulates circulating SAA levels by several hundred to a thousandfold. In order to be clinically useful, therefore, it is highly desirable that an assay for SAA be accurate over a concentration range of several orders of magnitude.

Marhaug (op. cit., 1983) compared a sandwich ELISA using polyclonal rabbit anti-AA and SAA and monoclonal mouse anti-SAA antibodies with an inhibition ELISA in which plates were coated with apoSAA, and test samples were incubated with monoclonal anti-SAA antibodies prior to addition to the wells. Both methods were affected by self-coating with SAA. Denaturation was not required and delipidation resulted in slightly reduced immunoreactivity. Neither assay provided the sensitivity required for clinically relevant measurements of SAA. Marhaug also described a radioimmunoassay, which he found to be more accurate than either ELISA. However, radioimmunoassay has numerous drawbacks inherent to use of radioactivity, and is thus not the method of choice for clinical measurement of SAA.

Dubois and Malmendier (*J. Immunol. Methods* 112, 71 (1988)) describe double sandwich ELISA methodology for measurement of human apolipoprotein S (probably identical to SAA) that utilized peroxidase conjugated anti-SAA antibodies to quantify apoS bound to wells coated with affinity purified anti-apoSAA. The sensitivity of this assay was adequate. However, the assay is very labor intensive because of the requirement for affinity purification of antibodies and conjugates. Moreover, the expense of the reagents is higher than is desirable for routine clinical use.

Zuckerman and Surprenant (*J. Immunol. Methods* 92, 37 (1986)) described a method in which SAA was directly coated from mouse serum at 4° C. in bicarbonate buffer pH 9.6. Like most of the previous assays, this assay expresses SAA concentrations in relative units rather than absolute amounts. As indicated above, expression of SAA concentrations in relative units limits comparison of values from samples obtained and assayed over a period of time and limits comparison of results among laboratories. Without such juxtaposition the clinical utility of any SAA assay is severely limited.

The methodology of Zuckerman and Surprenant is relatively quantitative for mouse SAA when samples were assayed at the same dilution. This method can be modified for measurement of SAA in human samples by using SAA-rich lipoprotein fractions to construct standard curves which would be more stable than those obtained with plasma. Samples within a group may then be assayed at the same dilution and the SAA concentration expressed in relative amounts of SAA-rich HDL.

However, the Zuckerman and Surprenant method has not proven suitable for clinical measurement of SAA in human plasma samples. In order to obtain meaningful comparisons, clinical samples must assayed over a SAA concentration range of several orders of magnitude. This necessitates assay of multiple sample dilutions of varying protein concentrations. Human plasma samples contain interfering proteins which affect binding in different ways at different sample dilutions. It is postulated that human SAA may interact more strongly with other plasma constituents than does mouse SAA. The method of Zuckerman and Surprenant contains no corrective provision for the variable interferences found in human plasma samples.

Moreover, SAA from human plasma has been found to bind less efficiently to microtiter plates than does SAA from mouse plasma or serum under the Zuckerman and Surprenant conditions. Another complication arises because the samples measured by Zuckerman and Surprenant were from mice which had experienced experimental inflammatory stimulation. Consequently SAA levels in the mice were high as compared with the relatively low SAA concentrations associated with human disease. It is believed that the sensitivity of the modified Zuckerman and Surprenant assay is therefore not sufficient to measure SAA levels in human clinical samples.

Antigen capture systems using a double sandwich solid phase ELISA with polyclonal rabbit anti-human SAA antiserum as the detection antibody have also proven ineffective for measurement of SAA in serum and plasma samples. The double sandwich solid phase ELISA yielded high results which were also variable. See, e.g., Marhaug (op. cit. 1983.) This method immobilizes antibody on casein-blocked microtiter plates and the analyte is added in solution. Moreover, the same amount of SAA bound to the casein-blocked plates whether or not antibody was immobilized on the plates. When some of the same samples were purified and assayed by the modified Zuckerman/Surprenant method, the SAA levels were observed to be much lower than the values from the double sandwich solid phase ELISA. These results suggest that the double sandwich solid phase ELISA for SAA was not accurate because of interactions between the SAA in the sample with the blocking agent, among SAA molecules in the sample, or between SAA molecules and other serum constituents such as albumin, fibronectin, or SAP.

Covalent binding of SAA to Co-Bind plates (Micro Membranes, 95 Orange Street, Newark, N.J. 01720) has also been ineffective. Purified SAA binds efficiently to the Co-Bind plates, showing greater levels of binding at pH 9.6 than at pH 7.2, which suggests that the increase in pH induces conformational changes exposing free amino groups which bound to the plates. Binding of purified SAA to the plates could be blocked, however, nonspecific binding was dramatically increased in plasma samples. Denaturation by heat or guanidine treatment of samples prior to capture was required to maximally expose determinants.

Direct binding of SAA from plasma to polyvinylchloride plates followed by delipidation with organic solvents is not sufficiently sensitive. The observation of Serban (U.S. Pat. No. 4,782,014) that SAA preferentially binds to plastic surfaces in the presence of a large excess of irrelevant protein is of limited utility in perfecting an immunoassay for SAA. Binding of SAA to the plastic surface must be controlled reproducibly and in such a way that a quantity directly proportional to the concentration of SAA in the test sample is bound. Such controlled and reproducible biding was not present in Serban.

Benditt et al. (op. cit., 1988) describe a competitive inhibition ELISA methodology in which plates are precoated with purified AA protein and the heat denatured samples are incubated with affinity purified apo-SAA antibodies. Subtractive competition assays measuring the ability of plasma samples to compete with antibody for binding to SAA antigen coated on plates was not sufficiently sensitive to detect large quantities of antigen and antibody are required for this assay.

Other proteins found in biological fluids have been similarly difficult to assay. IL-1 beta and CRP are examples of such proteins.

Although it has been relatively easy to measure IL-1 beta in culture supernatants by immunoassay, it has been difficult in plasma. Interference by plasma lipids and/or lipoproteins is indicated by Duff's laboratory (Eastgate, J. A., et al., Lancet, p. 706, Sep. 24, 1988) in which chloroform extraction is performed prior to measurement of IL-1 beta in the plasma of rheumatoid arthritis patients by ELISA. Accordingly, the present invention provides an improved assay for IL-1 beta.

The two clinical methods most frequently used for CRP are nephelometry and radial immunodiffusion. Both methods have a threshold of 5–8 µg/ml. The methodology of the present invention provides for measurement of CRP in the range of 1–10 µg/ml which may be clinically useful for rheumatoid arthritis patients.

In order to be useful for quantitative clinical measurements, it is highly desirable that an assay for any protein have the following characteristics:

1. Potential to measure the ligand in essentially absolute amounts rather than relative units.
2. Potential for accurate measurement of the ligand over a clinically relevant concentration range of the ligand;
3. Potential for automation of the assay.
4. Simple, reliable, inexpensive, and nonhazardous.

The ability to measurement absolute units permits comparison of results from samples obtained and/or measured over a period of time and comparison of results from different laboratories. It is also desirable that the test be capable of performance by multiple laboratory workers of relatively unsophisticated skill levels.

Thus, improved methods for measuring levels of proteins, especially those technically difficult to measure, are being sought because of the deficiencies of present methodologies.

SUMMARY OF THE INVENTION

Accurate and reproducible measurement of proteins having hydrophobic domains is achievable through the practice of the present invention. While not wishing to be bound by theory, it is thought that the hydrophobic domains of such proteins form non-specific hydrophobic interactions with various support media under the conditions of the methods of the present invention.

Accordingly, proteins which can be assayed in accordance with the present invention include those proteins which are capable of non-specific hydrophobic interactions with a desired support medium, particularly wherein such non-specific hydrophobic interactions are promoted in the presence of salt at an elevated pH and temperature. Such proteins are referred to herein as "adherent proteins." Accordingly, the methods of the present invention can be used to measure adherent proteins present in biological samples.

In accordance with the present invention, there is provided a method of determining the presence of amount of an adherent protein of interest in a sample which comprises:

a. contacting the sample at high salt concentration and elevated temperature with a support medium having an affinity for the adherent protein under conditions to promote binding of the adherent protein to the solid support;

b. contacting the support medium obtained in step (a) with at least one anti-ligand for the adherent protein under conditions to promote binding of the anti-ligand to the adherent protein;

c. detecting and measuring the amount of anti-ligand bound to the adherent protein;

d. either (i) relating the amount of anti-ligand determined in step (c) with the amount of anti-ligand measured for at least one control sample prepared in accordance with steps (a)–(c), said control sample comprising one or more unrelated proteins known to be free of the adherent protein, or (ii) relating the amount of anti-ligand measured in step (c) with the amount of anti-ligand measured for samples containing known amounts of adherent protein, said samples comprising purified adherent protein in a solution of one or more unrelated proteins and prepared in accordance with steps (a)–(c).

In accordance with the present invention, the salt concentration for binding an adherent protein of interest to a support medium may very from about 0.15 M to approximate saturation for the particular salt chosen; the pH may vary from about 8 to about 11; and the temperature may vary from about 40° C. to 65° C. The support medium may be solid or liquid. The anti-ligand may be any molecule which binds specifically to the adherent protein of interest, and any suitable method for detection of binding may be used.

Unrelated proteins are preferably proteins which do not cross-react immunologically with the adherent protein of interest. Such unrelated proteins may also aid in the binding of the adherent protein to a support medium in a manner similar to the manner in which the adherent protein would bind to the support medium if the biological fluid in which it is found were contacted therewith.

The application of this method to the measurement of serum amyloid A, apolipoprotein AI, apolipoprotein B, CRP, IFN-1 beta, TNF-alpha and albumin, respectively, is described in detail. The method is also applicable to other adherent proteins, particularly those which are similarly difficult to measure.

It is expected that the methods of the present invention will be useful in the assay of most proteins having one or more hydrophobic domains. The suitability of the methods of the present invention for assaying a particular protein, can be determined, e.g., by preparing control samples containing the protein of interest in accordance with the teachings herein and, then, determining as taught herein whether the protein in the control sample binds to the desired support medium.

BRIEF DESCRIPTION OF THE DRAWINGS

FIGS. 1A, 1B, 1C, and 1D show densitometric analysis of SDS-polyacrylamide (SDS is sodium dodecyl sulfate) gels of SAA purified as described in the Detailed Description of the Invention.

DETAILED DESCRIPTION OF THE INVENTION

Figure 2:
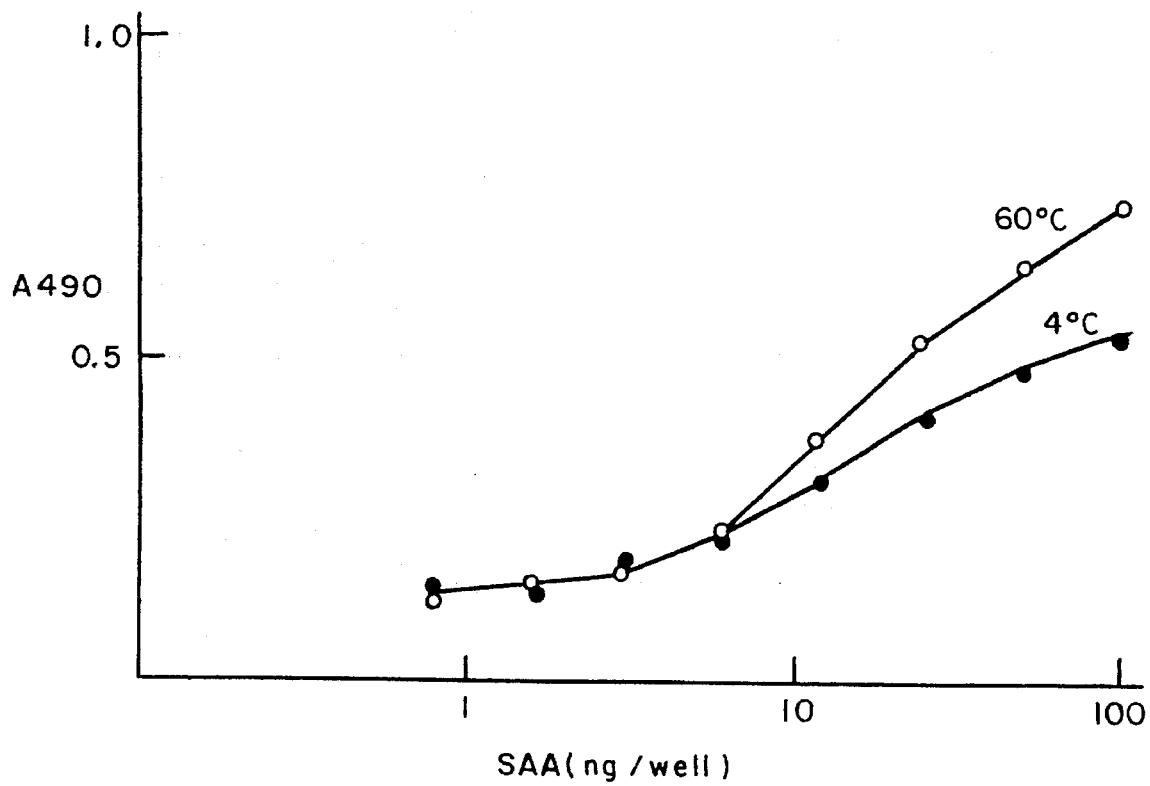
FIG. 2 shows the affect of temperature of SAA binding to microtiter plates.

The methods of the present invention are widely useful in determining the presence and concentration of adherent proteins in biological fluids, including lipophilic serum and plasma proteins, cytokines, globular serum and plasma proteins, and pentraxins. Such proteins include SAA, ApoAl, ApoB, CRP, IL-1 beta, TNF alpha, albumin and other proteins having a similar adherent nature.

The methods of the present invention are particularly useful in the measurement of the adherent lipophilic proteins found in HDL, LDL, VLDL and associated with other plasma proteins.

Because the accurate measurement of lipophilic proteins has been historically technically difficult, the methods of the present invention will be descried in connection with these lipophilic proteins, as well as other types of protein to show the wide usefulness of the subject methods.

Lipophilic proteins measured in accordance with the present invention are preferably those which are difficult to measure accurately because of the their conformation al changes and isotypic degeneracies. The method of the present invention is most preferably used to measure lipophilic proteins such as SAA, ApoAl, ApoB, tumor necrosis factor, interleukin-6, interleukin-1 beta, and similar proteins found in association with HDL, LDL, VLDL and other plasma proteins and which vary measurably during disease, trauma, or genetically pathological states. Other adherent proteins which can advantageously be measured by the present invention include CRP and albumin.

The methods of the present invention are preferably used to measure adherent proteins in large numbers of clinical samples which have been collected at varying times and by varying personnel. The present invention is most preferably used to provide justaposable data from more than one laboratory in large clinical studies.

In one preferred embodiment of the present invention, the method comprises contacting the sample to be measured with a support medium at high salt and high pH for a time sufficient for the adherent protein of interest to bind to the medium, under conditions that promote binding of the adherent protein to the support medium. The support medium is preferably a well or wells of a microtiter plate, a plastic bead, a chromatographic resin, a magnetized bead, or other suitable support which has affinity for the protein being measured. The support medium can also be a liquid medium in which more than one phase is present, or a liquid medium containing micellar structures. High salt concentration in accordance with the present invention is any salt concentration greater than physiological salt concentration, i.e., greater than about 0.15 M. High salt concentration in accordance with the present invention includes salt concentrations approaching saturation of the particular salt used. High pH in accordance with the present invention is any pH greater than about 8. High pH in accordance with the present invention includes pH of about 11. The conditions which promote binding between the adherent protein and the support medium can include varying the temperature, varying the concentration of the adherent protein, addition of other solutes, or modifying other parameters specific to particular adherent proteins.

After the adherent protein is bound to the support medium, an anti-ligand specific for the adherent protein is contacted with the adherent protein bound to the support medium. Any anti-ligand to the adherent protein may be used, as long as the anti-ligand is specific for the adherent protein. The anti-ligand is preferably an immunoglobulin, a receptor protein which binds specifically to the adherent protein, a membrane transport protein which binds specifically to the adherent protein, or similar molecule. The immunoglobulin is preferably a polyclonal antiserum from any appropriately inoculated animal or a monoclonal antibody specific or the adherent protein. A simple or complex carbohydrate which binds specifically to the adherent protein can also be used as an anti-ligand. In the case of lipophilic proteins, simple or complex lipids which bind specifically to the lipophilic protein can be used.

The amount of anti-ligand bound to the adherent protein affixed to the support medium is then determined using any suitable detection methods. Any detection method can be used, such as conjugated antibodies to the anti-ligand, conjugated anti-ligand-specific antibody fragments, conjugated biotin-avidin, and the like. Preferably the anti-ligand-specific antibodies, antibody fragment, or biotin-avidin are conjugated to fluorescent markers such as fluorescein or rhodamine, or to enzymes which catalyze the formation of products that can be quantified by their color or absorbance in the visible range, such as, $\beta$-galactosidase, alkaline phosphatase, or horseradish peroxidase.

In accordance with the present invention, the amount of anti-ligand bound to the adherent protein is then compared to a control sample or series of control samples, in order to determine the absolute amount of adherent protein present in the unknown sample. Any kind of control sample may be used, so long as it contains known amounts of a substance which can be empirically related to the adherent protein of interest. Preferably, the control samples will contain known amounts of the adherent protein of interest. More preferably, the control samples will contain known amounts of said adherent protein in purified or substantially purified form. Most preferably, the control samples will contain known amounts of the purified adherent protein along with a sufficient quantity of unrelated proteins to adjust the total protein concentration of the control sample to be about the same as that of the unknown samples.

The unrelated proteins are preferably proteins which do not cross-react immunologically with the adherent protein of interest. It is also preferred that the unrelated protein(s) aid in the binding of the adherent protein to the support medium in a manner analogous to which it would bind from biological fluid of interest. Unrelated proteins for use in the practice of the present invention include proteins found in biological fluids and bacterial and viral protein present during infections and other pathophysiological states.

When globular serum or plasma proteins are being assayed in accordance with the present invention, one or more different globular or serum proteins are used as the unrelated protein or proteins. More preferably, the unrelated proteins are albumin (except in the case wherein the adherent protein being measured is albumin) and immunoglobulin G. Most preferably, the unrelated proteins are albumin, again except in the case wherein the adherent protein being measured is albumin, and immunoglobulin G, both of the same taxonomic species as the adherent protein of interest, e.g., if the adherent protein is from humans, the unrelated proteins are most preferably from humans.

With respect to lipophilic proteins in particular, the methodology of the present invention differs from previously described assays in that the noncovalent interactions of lipophilic proteins with other plasma constituents are disrupted, permitting the direct coating of microtiter wells with a fraction of the lipophilic protein which is proportional to its concentration. In accordance with the present invention, lipophilic protein ligands are bound to microtiter plates in high salt at elevated temperature. Another feature of the present invention is the use of purified lipoprotein standard enriched in the ligand of interest and normalized to the total protein concentration of the samples. This methodology enables the simple, accurate and reproducible detection and measurement of lipophilic serum or plasma proteins in clinical samples on a large scale.

Although the present invention is useful in the assay of adherent proteins in general, it is especially useful for the assay of lipophilic proteins because it overcomes problems associated with previously available assays which make prior assays unsuitable for clinical measurement of lipophilic proteins. One embodiment of the present invention described herein includes immunoassay procedures for SAA and ApoAl that can be applied to serial monitoring of patients during large clinical trials. The features of these assays are (1) standard reference curves are constructed by addition of purified SAA-rich or ApoAl-rich lipoproteins to a solution of human IgG and albumin at concentrations corresponding to the test samples; (2) SAA or ApoAl ligands are coated on microtiter wells in high salt at elevated temperature; and (3) serial solutions are assayed simultaneously to insure that values for SAA or ApoAl concentration are obtained from dilutions in the linear range of the standard curve.

The assays of the present invention do not require a delipidation step, since the lipophilic protein of interest is coated onto the support medium, e.g., microtiter wells, at high temperature and high salt. Elimination of the delipidation step is advantageous, because delipidation of samples is labor-intensive and time-consuming. Moreover, delipidation can be a source of error in the level of lipophilic protein actually measured, since the process can degrade the protein or alter the conformation of antigenic sties.

Furthermore, the present invention offers significant advantages over known assays for lipophilic serum proteins in terms of sensitivity. For example, the concentration of SAA in patients with chronic conditions such as rheumatoid arthritis is lower than in experimental animals undergoing acute inflammation. (See, e.g., Zuckerman and Suprenant, supra). The present invention allows accurate and reproducible measurement of the low levels of SAA found in these patients, as well as allowing comparison of samples collected over a period of time and juxtaposition of results.

The assays of the present invention also use significantly less anti-SAA antiserum than do known procedures., e.g., Dubois and Malmendier (op. cit. 1988), since affinity purification of the antibodies is not required. Similarly, the present invention uses less antibody than the procedure of Saile et al., Clin. Chem. 34, 1988, which also employs affinity purified antibodies for capture and detection of human SAA in addition to requiring a sample delipidation step.

Examples 1 and 2 below illustrate the method of the present invention with respect to SAA. Example 3 illustrates the measurement of ApoA and ApoB. In Examples 4 through 6, the standard curves prepared using control samples, clearly demonstrate the usefulness of the methods of the present invention in assaying adherent proteins.

By means of specific anti-ligands and appropriate standards several adherent proteins of interest could be quantified in a single sample dilution distributed to numerous wells and samples in an individual well could be analyzed by using separable detection systems.

The invention will be further understood with reference to the following examples, which are purely exemplary in nature, and not meant to be utilized to limit the scope of the invention.

EXAMPLE 1

Preparation of Standard

SAA and ApoAl were isolated as HDL complex by ultracentrifugation from a pool of SAA-rich serum obtained from patients with gout and acute pneumonia (Roseff et al., 1987). After centrifugation at 2000×g, 4° C., for 15 minutes, solid KBr (reagent grade, FischerScientific, Medford, Mass.) was added to adjust the plasma to a density of 1.21 gm/cc. Aqueous Kbr solution, density 1.21 g/cc, was overlaid on up to 5 ml of adjusted plasma. The tubes were centrifuged in a SW41 rotor for 36 hrs., at 15° C. Seven equal fractions were removed sequentially from the tubes by aspiration. The fractions were dialyzed against phosphate buffered saline (PBS) and stored at 4° C. or −70° C. Repeated freeze-thawing was avoided.

The protein content of the fractions was determined using the BioRad (Richmond, Calif.) protein determination kit with crystalline bovine serum albumin (Calbiochem, San Diego, Calif.) as standard. The purity and physical characteristics of the SAA thus obtained was analyzed by polyacrylamide gel electrophoresis as described below (see FIG. 1). It has consistently been found that more than 80% of total plasma SAA is recovered with HDL following a single ultracentrifugation in KBr (FIG. 1).

FIG. 1(a) is the SDS-polyacrylamide gel electrophoretic analysis of SAA-rich plasma (1000 µg/ml) after ultracentrifugation of 5 ml of plasma in KBr, density 1.21 gm/cc for 40 hours at 15° C. Lanes 1 through 7 contain 100 pg each of protein. These results show that between 80 and 90% of total plasma SAA protein was recovered in the top three fractions after ultracentrifugation.

FIG. 1(b) is the comparison of SDS-polyacrylamide gel electrophoretic analysis of the top three fractions of a plasma pool from 10 healthy subjects (SAA, 4 µg/ml) with the top fraction of SAA-rich plasma. Lanes 1–3 contain 30 µg each of top fractions from normal plasma; Lane 4 contains 30 µg of top fraction of SAA rich plasma. This gel shows that no proteins of size similar to SAA were detected when plasma from healthy subjects was fractionated by the ultracentrifugation procedure described herein.

ApoAl content of the HDL standard fraction was determined in the same manner. Densitometric scanning showed that the HDL standard contained 9% ApoAl.

SDS Polyacrylamide Gel Electrophoresis

Presample buffer was prepared by mixing 1 ml of glycerol, 2.3 ml 10% SDS, 1.25 ml 0.5M Tris, pH 6.8, and 4.95 ml water. Loading buffer was prepared by mixing 930 µl of presample buffer, 50 µl of beta-mercaptoethanol and 52 µl of 0.1% bromophenol blue.

HDL and plasma fractions ere denatured by boiling for 5 minutes in loading buffer and the constituents were size fractionated on 11.4% polyacrylamide gels with a 5% stacking gel, both containing 6.4 M urea. Two sizes of gel have been utilized; the larger is 16×18 cm, 1.5 mm thick with 100 µg protein per lane and the smaller is 7.3×10.2 cm, 0.75 mm thick with 30 µg protein per lane. The larger gels were run at 250 volts with tap water cooling for 3 to 6 hours, the smaller at 75 volts with air cooling for 1.5–2 hours.

Gel bands of SAA were excised and the protein was eluted from the gel in the Schleicher and Schuell (VWR, Medford, Mass.) electroelution apparatus. The buffer employed was 0.025M Tris base, 0.19M glycine, 0.1% sodium dodecyl sulfate (SDS).

The percentage of SAA in the SAA/HDL fraction was determined densitometrically by scanning of individual lanes of Coomassie stained gels using the Electrophoresis Data Center (Helena Laboratories, Beaumont, Tex.). The relative SAA concentration was confirmed by ELISA analysis.

FIG. 1(c) is the SDS-polyacrylamide gel electrophoretic analysis of SAA/HDL standards by scanning of Coomassie blue stained gels. Lane 1: 100 ug SAA/HDL containing 37 ug SAA; Lane 2: 100 ug SAA/HDL containing 32 ug SAA by ELISA; Lane 3: 100 ug SAA/HDL containing 41 ug SAA by ELISA; Lane 4: 100 ug SAA/HDL containing 9 ug SAA by ELISA. Fraction 3 (FIG. 1C, Lane 4) was selected for use as a standard in subsequent ELISA experiments; it contained 9% SAA protein (Table I).

FIG. 1(d) is the SDS-polyacrylamide gel electrophoretic analysis of SAA electroeluted from Coomassie blue stained gels. Lane 1: 5 ug each of molecular weight markers; in descending order, ovalalbumin (43,000), alpha-chymotrypsinogen (25,700), betalactoglobin (18,400), lysozyme (14,300), bovine trypsin inhibitor (6,200) and insulin (3,000). Lane 2: Approximately 10 ug of SAA protein electroeluted from SAA bands as depicted in FIG. 1(a). When SAA was recovered from gel slices by electroelution, Coomassie blue remained tightly bound to the SAA monomer, which migrated as expected slightly ahead of the 14 kd molecular weight marker.

EXAMPLE 2

Measurement of SAA

Preparation of Antibodies to SAA

Electroeluted SAA at concentration of 200 ug/ml was emulsified with complete Freund's adjuvant and injected into rats at multiple sites (Wood et al., 1982). The rats were boosted at 3 week intervals, and serum was tested for an increase in antibody activity relative to preimmune serum by ELISA. The presence of SAA-specific antibodies were determined by the direct binding ELISA method of Zuckerman and Surprenant (1986).

The electroeluted SAA elicited antibodies at titers ranging from 1:100 to 1:10,000 with 3 weeks of immunization. The titers remained elevated for at least 12 weeks. It was necessary to absorb serum obtained later in the immunization regiment with normal serum or plasma. After absorption with plasma lacking detectable SAA (DeBeer et al., 1982), the antibodies reacted specifically with SAA-rich HDL, and did not react with HDL from normal plasma.

Rabbit antibodies were raised to human AA proteins as previously described (Linke et al., 1975). Rabbit antibodies to human SAA were purchased from Calbiochem (San Diego, Calif.) and a reference sample was kindly provided by Drs. A. Strachan and F. DeBeer (University of Stellenbosch, Tygerberg, South Africa).

ELISA of SAA

Anticoagulated plasma was stored frozen at −85° C. until analysis. A representative assay consisted of 4 microtiter plates, each containing the same 9 concentrations of SAA/HDL in triplicate wells. Plasma samples were diluted 1:10 by adding 10 μl of plasma to 90 μl of phosphate buffered saline (0.10M sodium phosphate, 0.15 M sodium chloride, pH 7.2 (PBS) in the wells of flexible polyvinyl chloride microtitration plates. Fifteen μl aliquots were transferred to wells containing 135 μl of 3M KBr in 0.1M sodium bicarbonate, pH 9.6 (1:100) dilution Immediately after mixing, 50 μl aliquots were transferred to another plate containing 100 μl of 3M KBr solution (1:300). Three additional three-fold dilutions (1:900, 1:2,700 and 1:8,100) encompass a linear range for SAA concentrations of up to 1,000 μg/ml. Fifty μl was discarded from the final plate.

Standard SAA/HDL preparation was serially diluted in a corresponding dilution (1:100, 1:300, etc.) of human IgG (Calbiochem, San Diego, Calif.) 13 mg/ml and albumin (Calbiochem, San Diego, Calif.) 45 mg/ml, stock concentrations. Six μl of SAA 1.4 mg/ml, 9% SAA was added to 200 μl of diluted IgG/albumin solution and after mixing, 100 μl was transferred to 100 μl of solution in 8 successive dilutions.

The wells of the microtiter plates were coated with SAA by overnight incubation at 60° C. The next day, the wells were emptied and nonspecific sites were blocked by addition of a 5% solution of dry milk in 0.02M phosphate buffer containing 0.05% Tween-20, pH 7.4, and incubation for 1 hour at room temperature. The plates were then washed three times with rinse buffer (0.02M phosphate, 0.05% Tween-20, pH 7.4).

The wells were incubated with 100 μl of a dilution of rat or rabbit polyclonal antiserum (1:300 or greater dilution) in rinse buffer for 90 minutes at 37° C. The plate was rinsed three times with rinse buffer, and 100 μl of a 1:1,000 dilution of peroxidase conjugated goat anti-rat or anti-rabbit IgG (Calbiochem) was added to each well. Incubation was carried out for 90 minutes at 37° C.

The plates were then washed nine times with rinse buffer. Substrate was prepared by dissolving 5.5 mg o-phenylenediamine dihydrochloride (PDA) in 10 ml citrate buffer (0.1M sodium citrate, 0.1M disodium monohydrogen phosphate pH 5). Immediately before addition to the microtiter wells, 33 μl of 3% hydrogen peroxide was added to the PDA solution. Aliquots of 100 ul of substrate solution were added to each well, and color development was monitored in the VMax Automated ELISA reader (Molecular Devices, San Diego, Calif.) at 450 nm. After about 5 minutes, 100 ul of 1M sulfuric acid was added and the plates were read at 490 nm. Data were analyzed by linear regression analysis of the standard curve obtained by plotting the log of ng/well SAA vs the absorbance at 490 nm. The coefficient of correlation of the points in the linear range of the curve was routinely >0.99. The average within plate coefficient of variation was less than 5%; the average between plate coefficient of variation was less than 20%.

Seven control samples and 16 samples comprises a single run, which was repeated to confirm values. This, together with the control values provided assurance that concentration values have been determined from the most appropriate dilutions (Table III). A value was always obtained from plate 1, 1:100 dilution. If the SAA value in ng/well as twice or greater the blank value for plate b, or thrice the value for plates c and d, the blank was subtracted from the gross ng/well and the net value was multiplied by the dilution factor to give the final SAA concentration in ug/ml for that plate.

Figure 4:
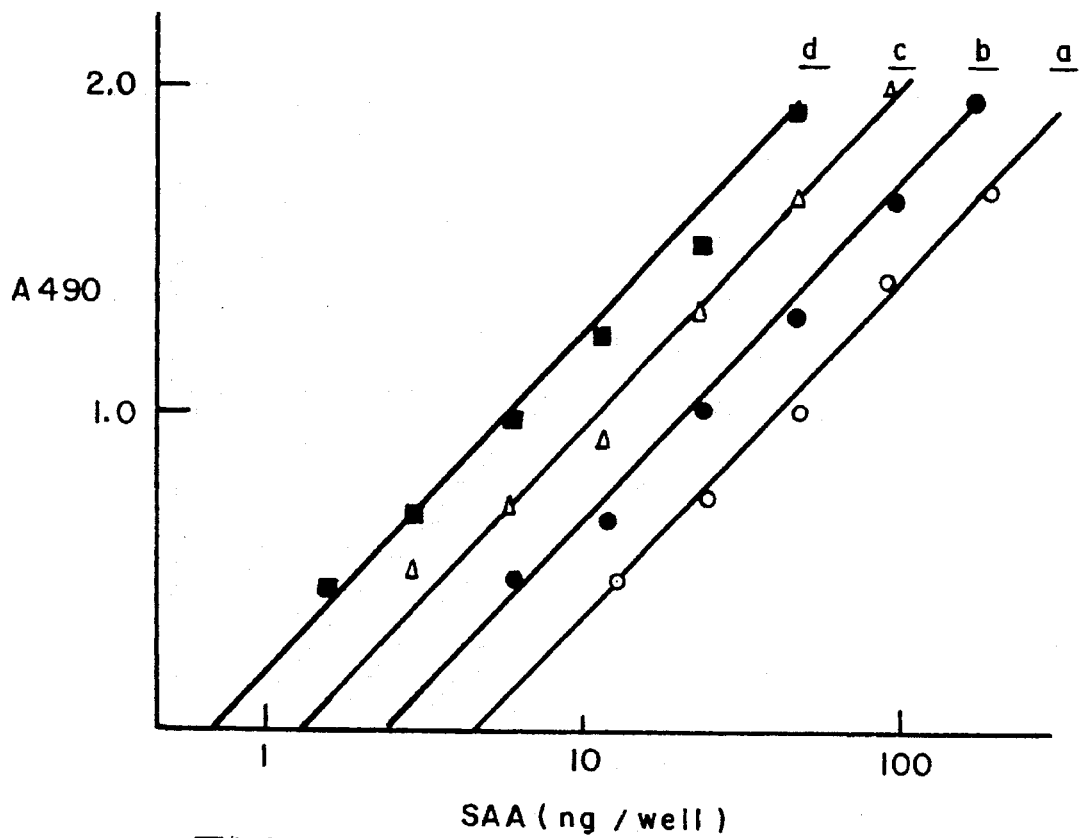
FIG. 4 depicts SAA standard curves prepared as described in the Detailed Description of the Invention.
Figure 5:
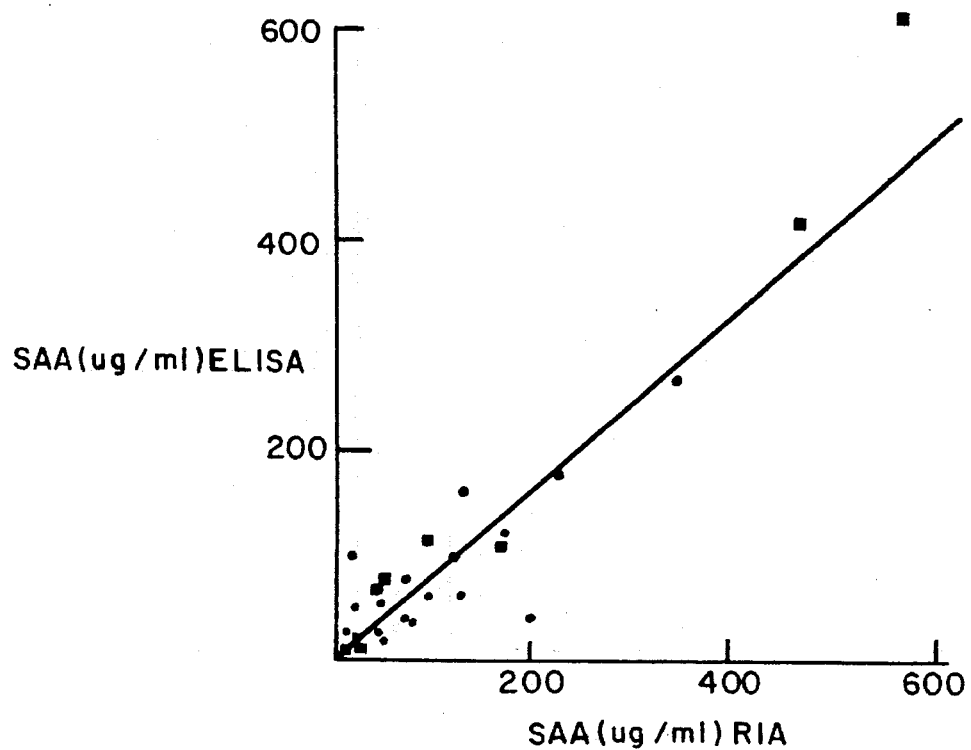
FIG. 5 is a comparison of the SAA ELISA of the present invention and a double antibody RIA.

It is desirable that the protein concentration of the standard curve be as similar as possible to the samples being tested if absolute, rather than relative, concentration values are needed. Standard curves for the SAA assay were linear over an approximately 20 fold range (FIG. 4). In FIG. 4, SAA/HDL in the amounts indicated was added to triplicate wells of plates a through d containing: a-1:100, b-1:300, c-1:900, d-1:2,700 dilution human IgG (13 mg/ml and albumin (45 mg/ml).

The sensitivity of the assay increased as the amount of competing plasma protein decreased, to <10 ng/well at a 1:2,700 dilution of plasma. The highest concentration of plasma that was routinely analyzed was a 1:100 dilution, and the minimum concentration of plasma SAA that could be detected by the method of the present invention was approximately 1 μg/ml.

The blank value, due to cross-reactivity of goat anti-rabbit conjugate with the human IgG, varied between 5 and 25 ng/well, according to efficacy of absorption of the conjugate serum with normal human plasma and with IgG and albumin. This value, generally on the order of 10 μg/ml is subtracted from each sample concentration value (Table III).

The coefficients of correlation of the standard curves are routinely ≧0.99.

Comparable results were obtained with commercial rabbit anti-SAA, rabbit anti-AA antiserum and rat anti-AA.

Effect of Temperature on SAA Binding

Heat was found to promote proportional and reproducible coating of SAA to wells (FIGS. 2 and 3). SAA/HDL standard was serially diluted in bicarbonate solution, pH 9.6 to give the amounts of SAA per well shown in FIG. 2. The plates were sealed and incubated at 4° C. —O— or 60° C. —O—. The amount of SAA bound by the wells was proportional to the absorbance at 490 nm. The average coefficient of variation of triplicate wells was less than 5 percent.

FIG. 2 shows that coating the wells with the SAA/HDL standard protein overnight at 60° C. in bicarbonate solution pH 9.6 enhanced binding and/or exposure of antigenic determinants as compared with overnight binding at 4° C. Direct binding of SAA from serum and plasma samples was also increased at elevated temperatures (Table II). However, the amount of SAA bound to wells from serum or plasma containing a greater amount of SAA was much less than from isolated HDL fractions, indicating a substantial dampening effect of serum components upon binding.

Effect of Salt on SAA Binding

Figure 3A:
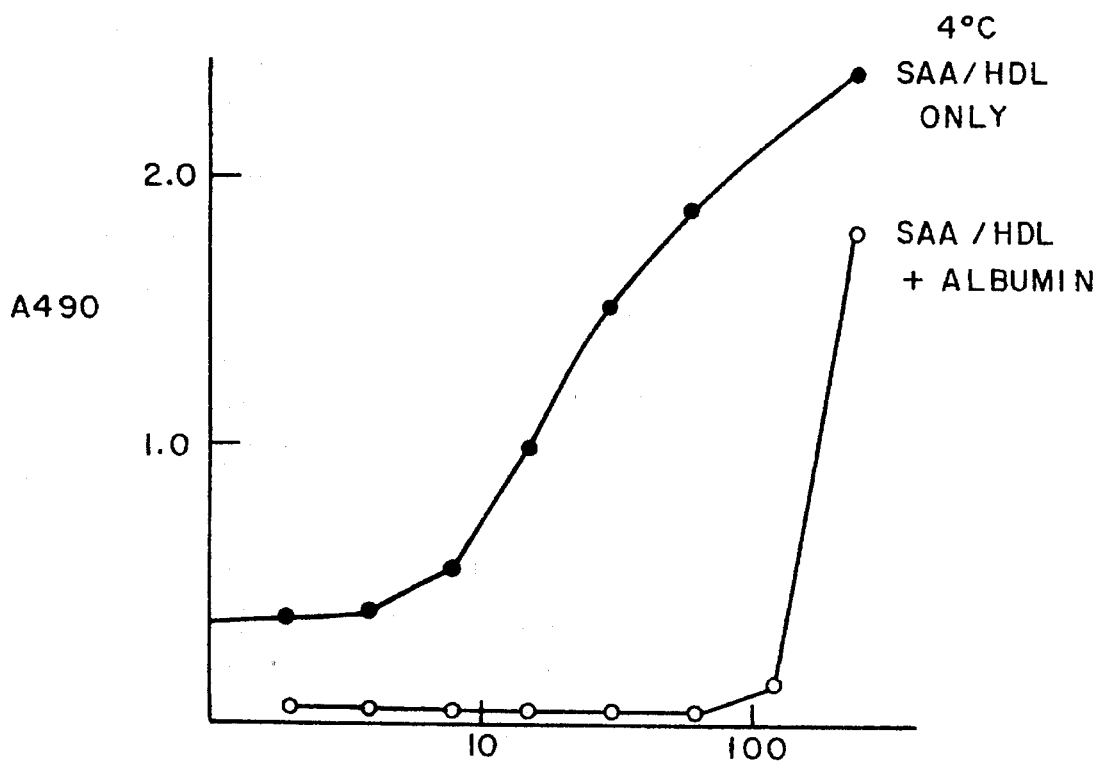
FIGS. 3A and 3B show inhibitory effect of albumin on SAA binding to wells of microtiter plates and its reversal by heating in the presence of salt.

Salt was also found to promote proportional and reproducible coating of SAA to wells. FIG. 3 shows the inhibitory effect of albumin on SAA binding to wells of microtiter plates and its reversal by heating in the presence of salt. In FIG. 3(a), a mixture of SAA/HDL standard (1,200 ng/ml) and albumin (10 μg/ml) were serially diluted in bicarbonate solution, pH 9.6, and wells were coated by overnight incubation at 4° C. —O—. SAA/HDL standard only was incubated overnight at 4° C. —O—.

Figure 3B:
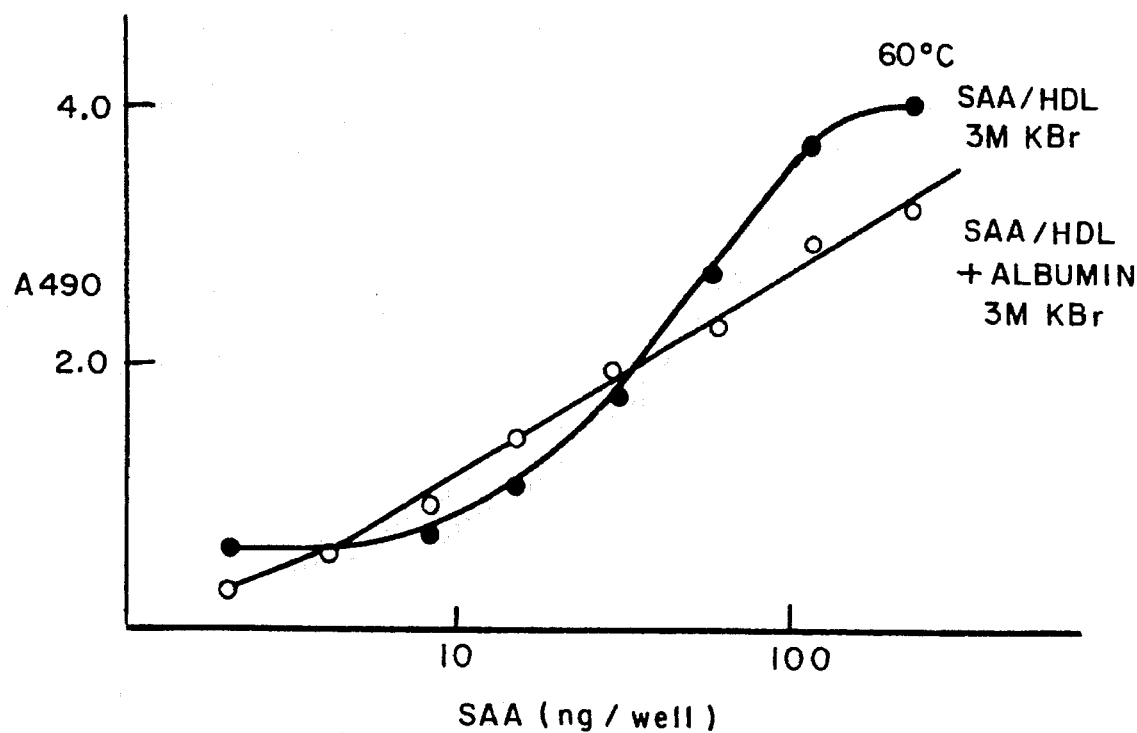

In FIG. 3(b), SAA/HDL with and without albumin was diluted as described for FIG. 3(a), but coating was carried out by incubation at 60° C. in 3M KBR overnight.

Binding of SAA to wells was inhibited in the presence of albumin, particularly at 4° C. (FIG. 3a). Greater binding of SAA from HDL fractions and from plasma was observed when plasma was diluted in 3M KBr and binding was carried out at 60° C. Salt and elevated temperature were observed to diminish the inhibitory effect of albumin on SAA binding (FIG. 3B).

EXAMPLE 3

Measurement of ApoAI and ApoB

A. ApoAI

Anticoagulated plasma was stored frozen at −85° C. until analysis. A representative assay consisted of 4 mircotiter plates, each plate containing the same sample concentration in triplicate wells. Plasma samples were diluted 1:20 by adding 10 μl of plasma to 190 μl of PBS in the wells of microtitration plates. Ten μl of the first dilution was further diluted into 190 μl PBS, to yield a 1:400 dilution of the original sample. Ten μl aliquots of the 1:400 dilution was transferred to triplicate wells containing 190 μl of 3M KBr in 0.1 M sodium bicarbonate, pH 9.6 (1:8,000) dilution. Immediately after mixing, 100 μl aliquots were transferred to another plate containing 100 μl of 3M KBr solution (1:16,000). Two additional two-fold dilutions (1:32,000 and 1:64,000) encompass a linear range for ApoAl concentrations of up to 7 mg/ml. One hundred μl was discarded from the final plate.

Standard ApoAl/HDL preparation was serially diluted in a corresponding dilution (1:8,000, 1:16,000, etc.) of human IgG (Calbiochem. San Diego, Calif.) 13 mg/ml and albumin (Calbiochem, San Diego, Calif.) 45 mg/ml, stock concentrations. 5.2 μl of HDL containing ApoAl 1.5 mg/ml, 9% ApoAl was added to 200 μl of diluted IgG/albumin solution and after mixing, 100 μl was transferred to 100 μl of solution in 11 successive dilutions.

The wells of the microtiter plates were coated with ApoAl by overnight incubation at 60° C. The next day, the wells were emptied and nonspecific binding sites are blocked with a 5% solution of dry milk in 0.02M phosphate buffering containing 0.05% Tween 20, pH 7.4, by incubating for 1 hour at room temperature. The plate was washed three times with rinse buffer without dry milk.

The wells were incubated with 100 μl of a dilution of rabbit polyclonal anti-ApoAl antiserum (Calbiochem, LaJolla, Calif.) (1:3,000 dilution) in rinse buffer for 90 minutes at 37° C. The plate was rinsed three times with rinse buffer, and 100 μl of a 1:1,000 dilution of peroxidase conjugated goat anti-rabbit IgG was added to each well. Incubation was carried out for 90 minutes at 37° C.

The plates were then washed nine times with rinse buffer. Substrate was prepared by dissolving 5.5 mg o-phenylenediamine dihydrochloride (PDA) in 10 ml citrate buffer (0.1M sodium citrate, 0.1M disodium monohydrogen phosphate pH 5). Immediately before addition to the microtiter wells, 33 μl of 3% hydrogen peroxide was added to the PDA solution. Aliquots of 100 ul of substrate solution were added to each well, and color development was monitored in the VMax Automated ELISA reader (Molecular Devices, San Diego, Calif.) at 450 nm. After about 5 minutes, 100 ul of 1M sulfuric acid was added and the plates were red at 490 nm. Data were analyzed by linear regression analysis of the standard curve obtained by plotting the log of ng/well SAA vs the absorbance at 490 nm. The coefficient of correlation of the points in the linear range of the curve was routinely <0.99. The average within plate coefficient of variation was less than 5%; the average between plate coefficient of variation was less than 20%.

Figure 6:
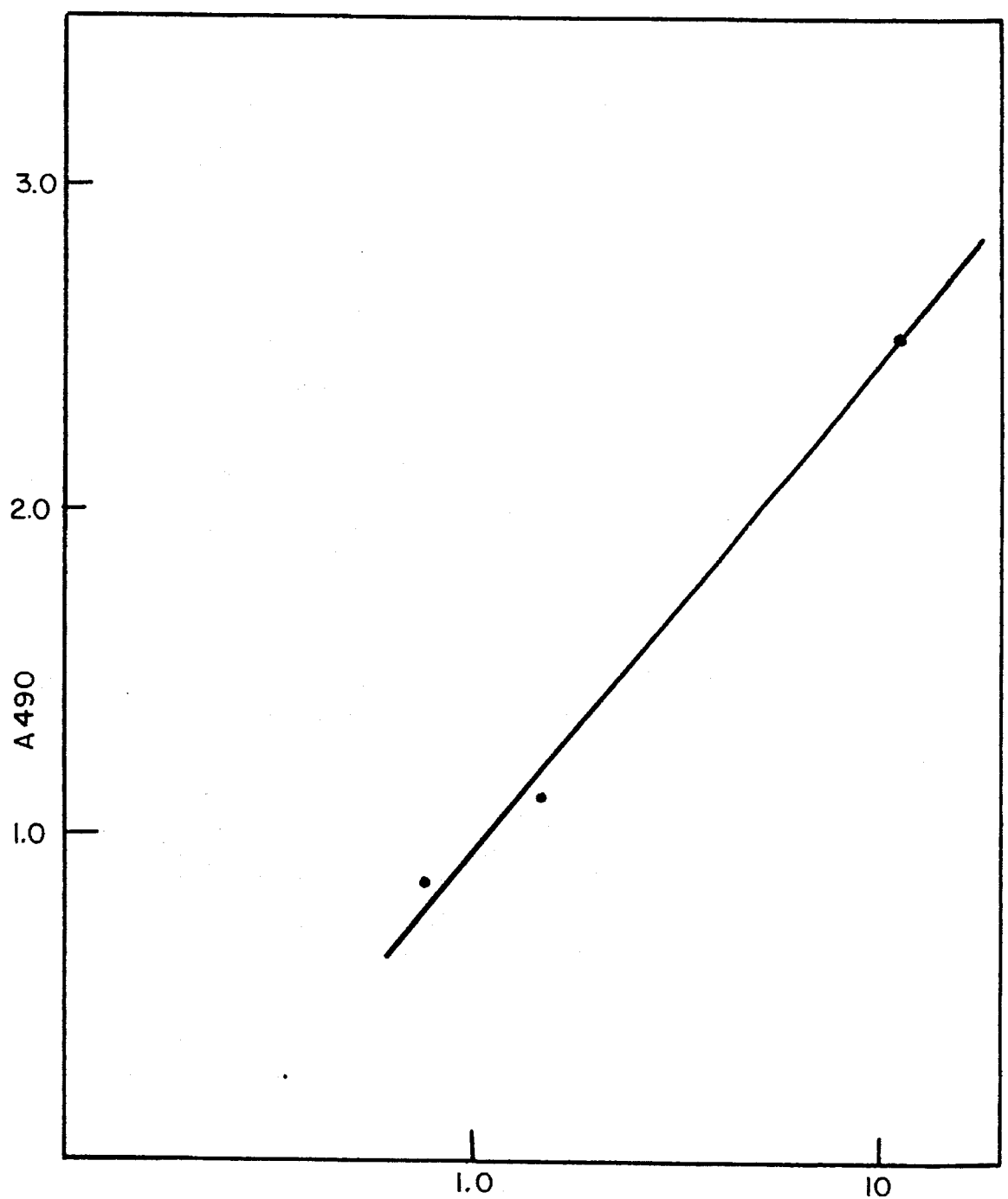
FIG. 6 is a representative standard curve for the ApoAl ELISA of the present invention, prepared as described in the Detailed Description of the Invention.

Results of the ApoAl assay are shown in Table IV. FIG. 6 is a standard curve for the ApoAl ELISA of the present invention.

Figure 7:
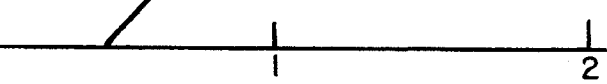
FIG. 7 is a comparison between the ApoAl ELISA of the present invention and a conventional immunoturbidimetric assay.

FIG. 7 shows a comparison of the ELISA of the present invention with a conventional immunoturbidimetric assay for ApoAl. The immunoturbidimetric assay was performed using a kid from Sigma Diagnostics (St. Louis, Mo.).

B. ApoB

In the ApoB assay, the procedure was as described in Example 3.A. above for the standard ApoAl/HDL preparation, except that an LDL preparation from Calbiochem was used as standard. Primary and secondary antibody concentrations were 1:1,000 and 1:5,000.

Figure 8:
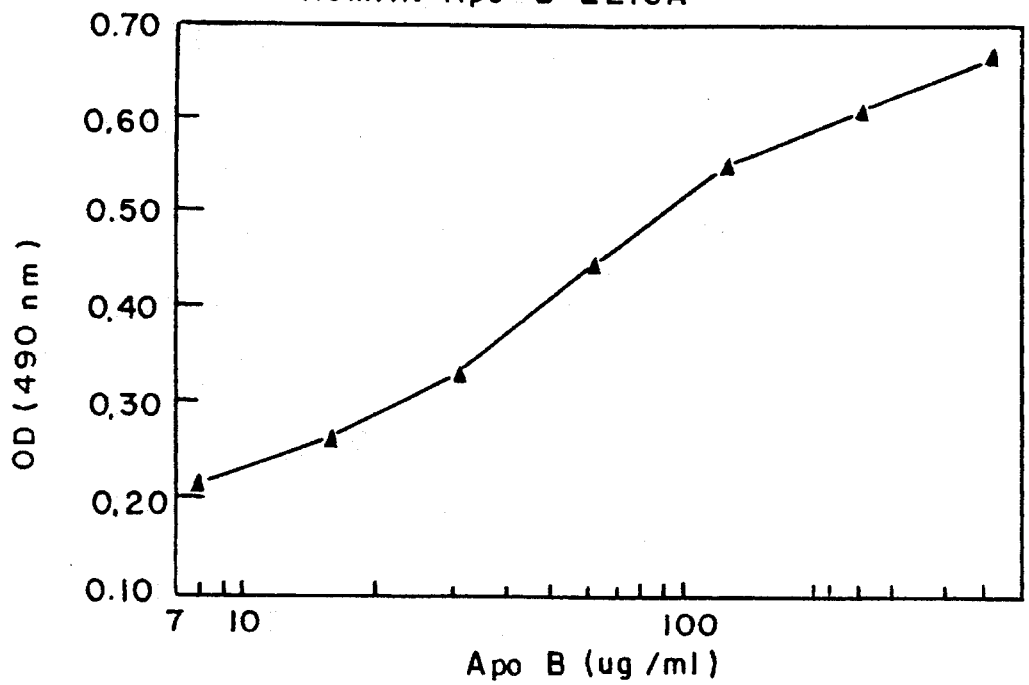
FIG. 8 shows a standard curve for an ApoB ELISA of the present invention.

FIG. 8 shows a standard curve for the ApoB ELISA of the present invention.

EXAMPLE 4

Measurement of Cytokines: IL-1 beta and TNF alpha

In the measurement of the cytokines, IL-1 beta and TNF alpha, procedures were as described for the standard apoAl/

HDL preparation in Example 3, above except that purified recombinant generated cytokines were used and that IgG/albumin was not used in the coating buffer except as indicated for IL-1, where it was used at 1:100 of the stock concentrations. The dilutions for the primary and secondary antibodies were 1:1,000.

Figure 9:
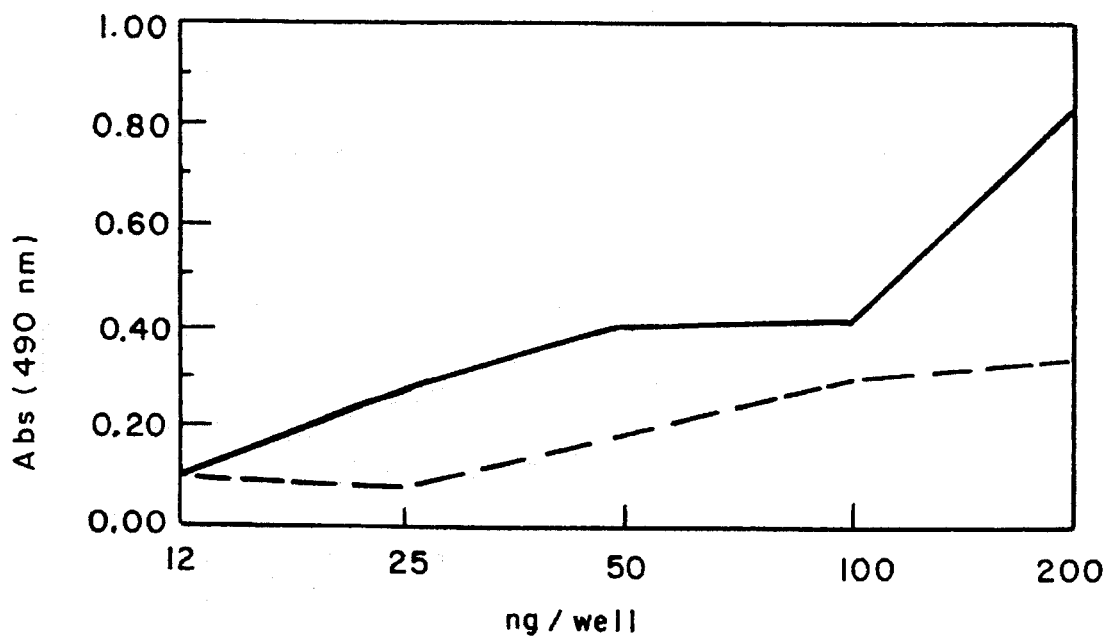
FIG. 9 shows standard curves prepared in accordance with the present invention for IL-1 beta in the presence and absence of IgG/albumin.
Figure 10:
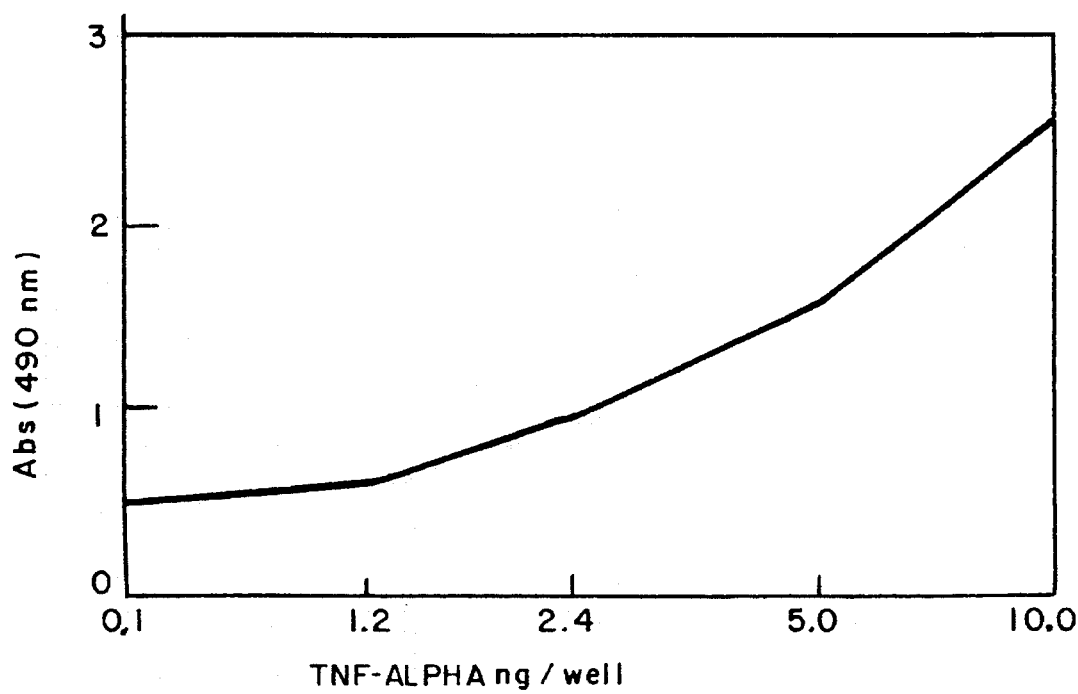
FIG. 10 shows a standard curve prepared in accordance with the present invention for TNF/alpha.

FIG. 9 shows standard curves for control samples containing IL-1 beta in the presence and absence of IgG/albumin. FIG. 10 shows a standard curve for TNF-alpha.

EXAMPLE 5

Measurement of CRP

In the following assay, primary and secondary antibody concentrations were 1:1,000 to 1:5,000.

Purified CRP was purchases from Sigma and rabbit antibodies to purified CRP from Calbiochem.

Figure 11A:
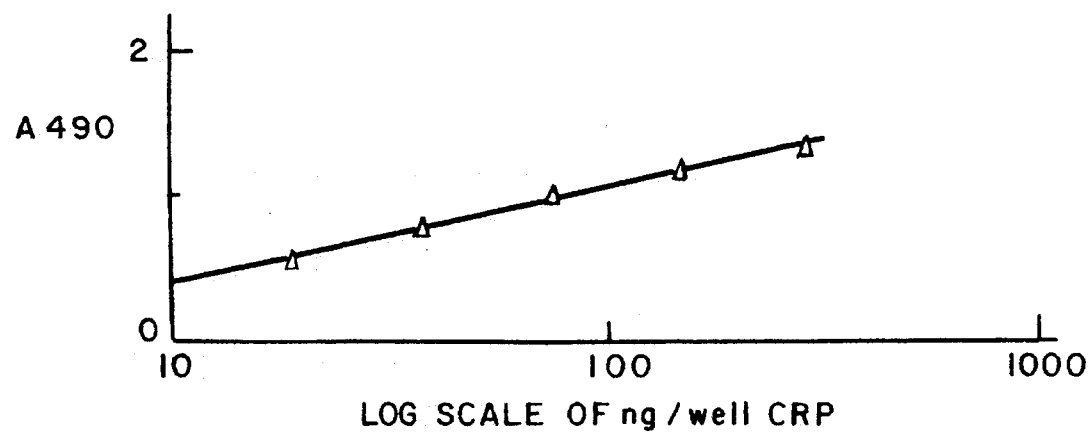
FIG. 11 shows standard curves obtained in accordance with the present invention for purified human CRP in the presence (FIG. 11A) and absence (FIG. 11B) of purified human IgG and albumin.
Figure 11B:
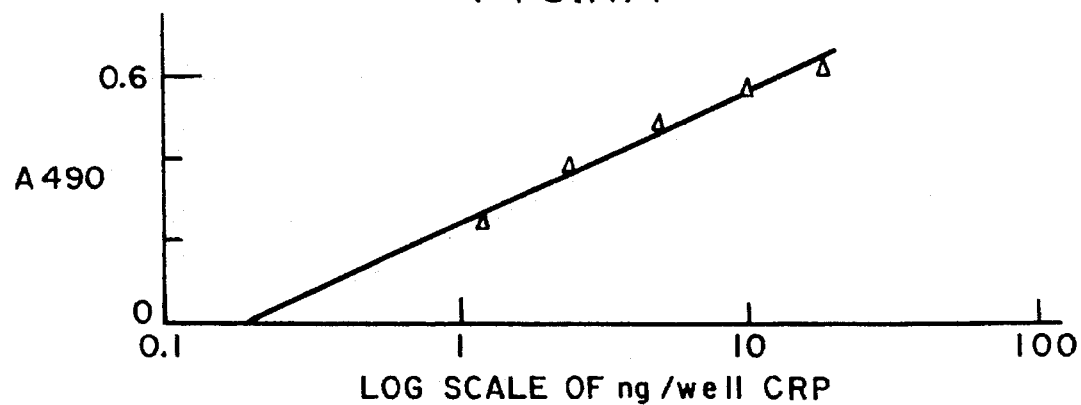

FIG. 11 shows standard curves obtained for control samples containing purified human CRP in the presence (FIG. 11A) and absence (FIG. 11B) of purified human IgG and albumin. Using the standard curve with albumin and IgG, clinically reasonable values were obtained i.e. CRP was not detectable in normal plasma and was 11.8 ug/ml in the plasma of a rheumatoid arthritis patient. The plasma samples were diluted 1:100.

EXAMPLE 6

Measurement of Albumin

In the following assay, primary and second antibody concentrations were 1:1,000 and 1:5,000.

Purified human albumin and rabbit antibodies to albumin were purchased from Calbiochem.

Figure 12A:
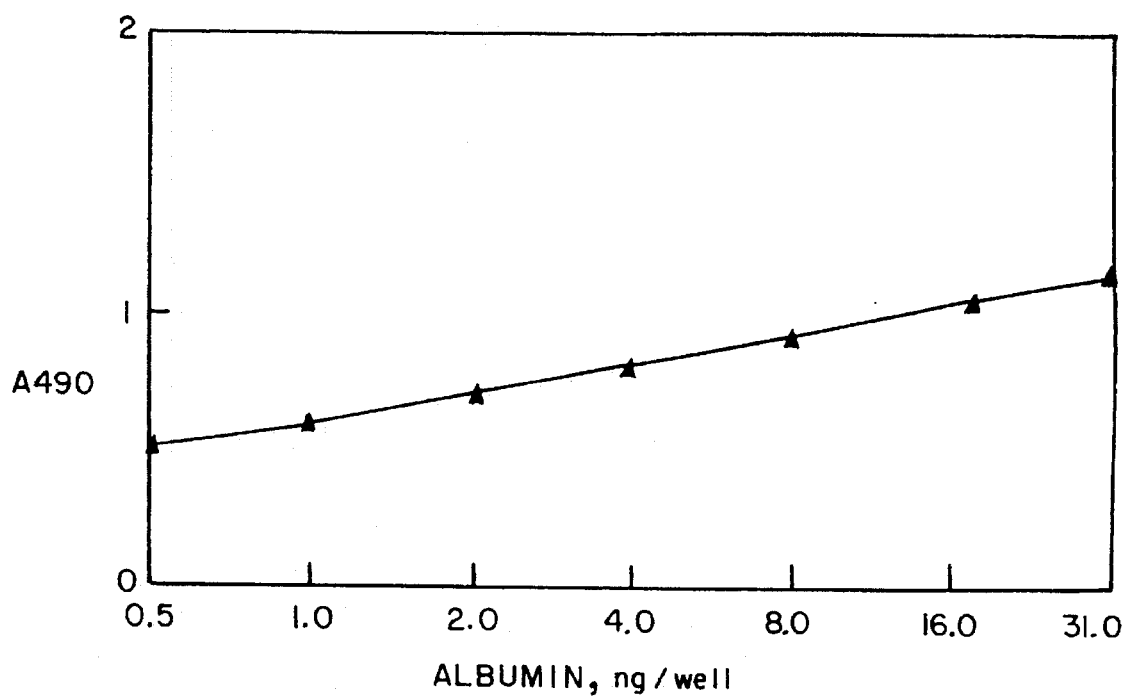
FIG. 12 shows standard curves obtained in accordance with the present invention for purified serum albumin in the presence (FIG. 12A) and absence (FIG. 12B) of purified human IgG.
Figure 12B:
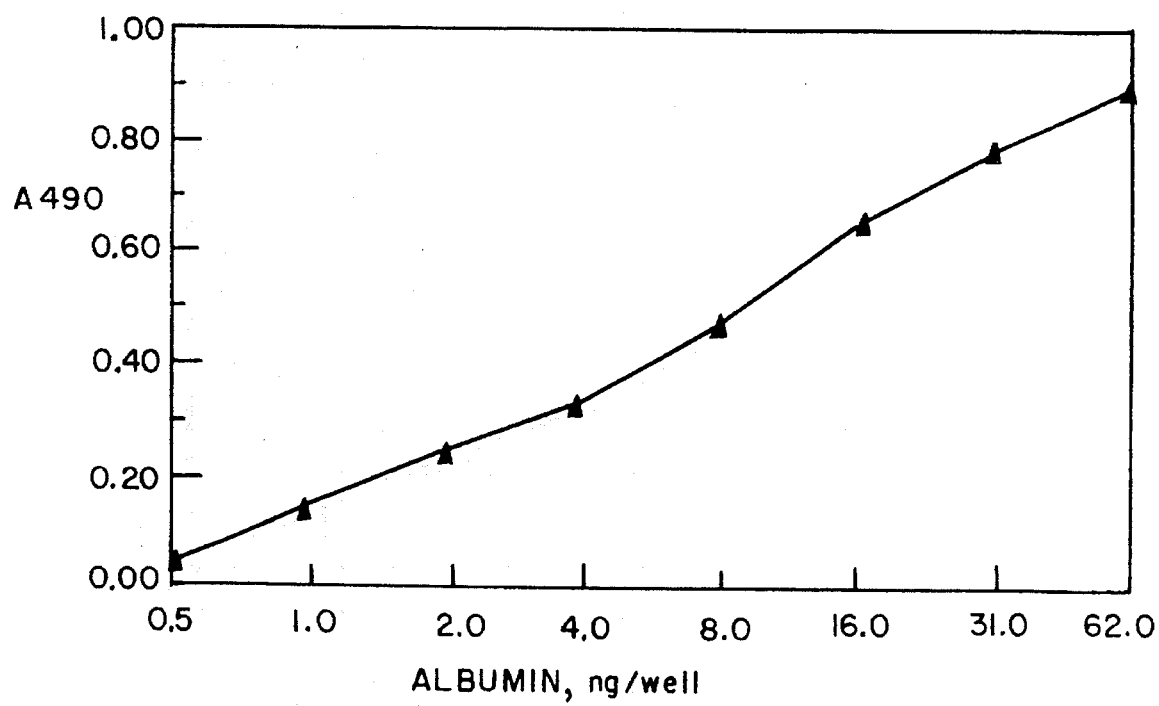

FIG. 12 shows standard curves obtained for control samples containing purified serum albumin in the presence (FIG. 12A) and absence (FIG. 12B) of purified human IgG.

Table V shows values obtained by a preliminary ELISA for albumin concentrations in plasma from a healthy individual (NHP) and a rheumatoid arthritis patient (RA). In order to optimize this ELISA, it is desirable to add other unrelated proteins, such as lipoprotein, in addition to IgG to the standard curve in order to obtain absolute values for albumin, because values obtained in the presence of IgG were lower than in the absence of IgG. The plasma samples were diluted 1:40,000.

TABLE I

Comparison of SAA content determined by gel scanning and by ELISA

| SAA/HDL (ng analyzed) | % SAA |
|---|---|
| | ELISA |
| 700 | 8, 12, 9 |
| 350 | 6, 14, 8, 10 |
| 185 | 5, 13, 8, 9 |
| 88 | 4, 14, 12, 7 |
| Average SAA content | 9.3 ± 3.1% |
| | Gel Scan |
| 100 | 9.3 |

SAA content of lane 4, FIG. 2B, was compared by ELISA with SAA/HDL standard, 37% SAA. Coating of wells was carried out at 4° C. in bicarbonate buffer, pH 9.3, lacking KBr. Gel scanning of Coomassie stained gel was carried out as described in the Methods Section.

TABLE II

Effect of temperature on SAA binding from plasma samples.

| SAA concentration | 4° C. | A 490 60° C. |
|---|---|---|
| 4 ug/ml | 0.18 | 0.24 |
| 32 | 0.15 | 0.28 |
| 112 | 0.27 | 0.36 |
| 585 | 0.55 | 0.42 |
| 1000 | 0.59 | 0.68 |

Plasma samples were diluted 1:10 in PBS and then 1:10 in KBr bicarbonate buffer, pH 9.6. Incubation was carried out overnight at indicated temperature, and the amount of SAA bound was quantified by measurement of absorbance at 490 nm after blocking and incubation with antibodies as described in the Methods Section.

TABLE III

SAA Direct Binding ELISA Data and Calculations

| | SAA (ng/well) | | | | | | | |
|---|---|---|---|---|---|---|---|---|
| | Run 1 | | | | Run 2 | | | SAA |
| Sample | a | b | c | d | a | b | c | d (ug/ml) |
| 1 | 17 | 10 | 8 | 4 | 19 | 9 | 6 | 3 6, 9 |
| 2 | 17 | 8 | 6 | 3 | 16 | 8 | 5 | 3 6, 6 |
| 3 | 16 | 8 | 6 | 3 | 16 | 8 | 5 | 3 5, 6 |
| 4 | 15 | 8 | 6 | 3 | 15 | 8 | 5 | 3 4, 5 |
| 5 | 15 | 8 | 6 | 3 | 14 | 8 | 5 | 3 3, 4 |
| 6 | 16 | 7 | 6 | 3 | 14 | 8 | 5 | 3 5, 4 |
| 7 | 16 | 8 | 6 | 3 | 14 | 8 | 6 | 3 5, 4 |
| 8 | 28 | 14 | 9 | 4 | 28 | 13 | 7 | 4 17, 24, 18, 21 |
| 9 | 31 | 15 | 10 | 4 | 42 | 17 | 9 | 4 20, 27, 32, 33 |
| 10 | 20 | 10 | 9 | 4 | 25 | 11 | 7 | 4 9, 15 |
| 11 | 14 | 7 | 6 | 3 | 14 | 8 | 5 | 3 3, 4 |
| 12 | 14 | 8 | 6 | 3 | 16 | 8 | 6 | 3 3, 6 |
| 13 | 48 | 29 | 15 | 6 | 85 | 35 | 16 | 7 37, 69, 99, 104 75, 87, 108 |
| 14 | 14 | 9 | 7 | 4 | 16 | 9 | 6 | 3 3, 6 |
| 15 | 15 | 8 | 7 | 4 | 15 | 9 | 6 | 3 4, 5 |
| 16 | 14 | 8 | 6 | 3 | 16 | 8 | 6 | 3 3, 6 |
| 17 | 44 | 17 | 10 | 4 | 41 | 16 | 7 | 4 33, 33, 31, 30 |
| 18 | 168 | 50 | 20 | 8 | 117 | 37 | 12 | 5 157, 132, 144 107, 93 |
| 19 | 112 | 32 | 17 | 6 | 57 | 20 | 9 | 5 101, 78, 117 47, 42, 45 |
| 20 | 99 | 58 | 37 | 20 | 143 | 68 | 35 | 20 294, 486 279, 459 |
| 21 | 145 | 123 | 61 | 31 | 194 | 131 | 53 | 31 513, 783 441, 756 |

TABLE IV

Comparison of ApoAl Direct Binding ELISA and Turbidimetric Assay

| Sample | Kit (mg/ml) | ELISA (mg/ml) |
|---|---|---|
| 1. NHP | 1.74 | 2.50 |
| 2. MED | 0.76 | 0.75 |
| 3. APP | 1.08 | 0.64 |
| 4. P1 | 1.00 | 0.97 |
| 5. P2 | 1.36 | 1.50 |
| 6. Kit Control I | 0.97 | 1.04 |
| 7. Kit Control II | 1.50 | 1.56 |

TABLE V

Albumin Direct Binding ELISA: Normal Human Plasma and Plasma From Rheumatoid Arthritis Patient

| | Sample in mg/ml | | |
|---|---|---|---|
| | NHP | RA 1578 | IgG |
| Curve w/o IgG | 8.65 | 10.64 | |
| Curve w/IgG | 5.73 | 7.22 | 0.05 |

It is understood that the examples and embodiments described herein are for illustrative purposes only, and that various modifications or changes in light thereof that will be suggested to persons skilled in the art are to be included in the spirit and purview of this application and the scope of the approved claims.

What is claimed is:

1. A method of determining the amount of an adherent protein in a sample, the adherent protein being capable of forming a non-specific hydrophobic interaction with a support medium, the method comprising:

(a) contacting the sample of high salt concentration wherein the salt concentration is from about 0.15M to about saturation with a support medium having an affinity for the adherent protein under conditions to effect disruption of noncovalent interactions of the adherent proteins with other constituents of the sample and binding of a fraction of the adherent protein which is proportional to its concentration to the support medium;

(b) contacting the support medium obtained in step (a) with at least one anti-ligand for the adherent protein under conditions to promote specific binding of the anti-ligand to the adherent protein;

(c) detecting and measuring the amount of anti-ligand bound to the adherent protein; and (d) either (i) relating the amount of bound anti-ligand determined to step (c) with the amount of bound anti-ligand measured for at least one control sample prepared in accordance with steps (a)–(c), said control sample comprising one or more unrelated proteins known to be free of the adherent protein, or (ii) relating the amount of bound anti-ligand measured in step (c) with the amount of anti-ligand measured for samples containing known amounts of adherent protein, said samples comprising purified adherent protein in a solution of one or more unrelated proteins, and prepared in accordance with steps (a)–(c).

2. The method of claim 1, wherein the adherent protein is a lipophilic serum protein, a cytokine or a globular serum or plasma protein or a pentraxin.

3. The method of claim 2, wherein the lipophilic serum protein is one associated with HDL, LDL, or VLDL.

4. The method of claim 3, wherein the lipophilic serum protein is one associated with HDL.

5. The method of claim 2, wherein the lipophilic serum protein is serum amyloid A, apoprotein Al, apoprotein B, tumor necrosis factor, or interleukin-6.

6. The method of claim 1, wherein the temperature is from about 40° C. to about 65° C.

7. The method of claim 6, wherein the pH of step (a) is from about pH 8 to about pH 11.

8. The method of claim 1, wherein the unrelated protein is a globular serum protein.

9. The method of claim 1, wherein the unrelated proteins are immunoglobulin G and serum albumin.

10. The method of claim 1, wherein the unrelated protein is serum albumin.

11. The method of claim 1, wherein the support medium comprises a solid medium.

12. The method of claim 11, wherein the solid medium comprises microtiter plates, plastic beads, resins, or magnetic beads.

13. The method of claim 1, wherein the support medium comprises a liquid medium.

14. The method of claim 1, wherein the anti-ligand is a polyclonal antiserum, a monoclonal immunoglobulin, a receptor molecule, or a lipid transport molecule.

15. The method of claim 1, wherein the anti-ligand comprises an anti-ligand-specific antibody an anti-ligand-specific antibody fragment, or biotin-avidin conjugated to a label.

16. The method of claim 15; wherein the conjugated anti-ligand-specific antibody, the conjugated anti-ligand-specific antibody fragment or the conjugated biotin-avidin is conjugated to a fluorescent label.

17. The method of claim 16, wherein the fluorescent label is fluorescein or rhodamine.

18. The method of claim 15, wherein the label is an enzyme.

19. The method of claim 18, wherein the label is β-galactosidase, alkaline phosphate, or horseradish peroxidase.

20. A method of determining the presence of an adherent protein in a sample, the adherent protein being capable of forming a non-specific hydrophobic interaction with a support medium, the method comprising:

(a) contacting the sample at high salt concentration with a support medium having an affinity for the adherent protein under conditions to effect disruption of noncovalent interactions of the adherent proteins with other constituents of the sample and binding of a fraction of the adherent protein which is proportional to its concentration to the support medium;

(b) contacting the support medium obtained in step (a) with at least one anti-ligand for the adherent protein under conditions to promote specific binding of the anti-ligand to the adherent protein; and (c) detecting anti-ligand bound to the adherent protein.

* * * * *